(12) United States Patent
Veeder (10) Patent No.: US 7,798,141 B2
(45) Date of Patent: Sep. 21, 2010

(54) MANUALLY ADJUSTABLE NASAL CAVITY DILATOR

(76) Inventor: Matthew P. Veeder, 16109 Evanston Ave. N., Shoreline, WA (US) 98133-5648

( * ) Notice: Subject to any disclaimer, the term of this patent is extended or adjusted under 35 U.S.C. 154(b) by 1245 days.

(21) Appl. No.: 11/198,659

(22) Filed: Aug. 5, 2005

(65) Prior Publication Data
US 2007/0028917 A1 Feb. 8, 2007

(51) Int. Cl.
A61M 15/00 (2006.01)
A61M 16/00 (2006.01)
A61F 9/00 (2006.01)

(52) U.S. Cl. .............. 128/200.24; 128/201.18; 128/858

(58) Field of Classification Search ......... 128/206.11, 128/200.24, 207.13, 207.18, 200.26, 206.25, 128/207.11, 207.17, 848, 858, 912, DIG. 26
See application file for complete search history.

(56) References Cited

U.S. PATENT DOCUMENTS

| 4,414,977 | A | | 11/1983 | Rezakhany | 128/342 |
|---|---|---|---|---|---|
| 4,535,772 | A | | 8/1985 | Sheehan | 606/218 |
| 5,533,499 | A | | 7/1996 | Johnson | 128/200.24 |
| 5,533,503 | A | | 7/1996 | Doubek et al. | 128/200.24 |
| 5,669,377 | A | | 9/1997 | Fenn | 128/200.24 |
| 5,706,800 | A | | 1/1998 | Cronk et al. | 128/200.24 |
| 5,735,272 | A | | 4/1998 | Dillion et al. | 128/207.18 |
| 5,755,232 | A | | 5/1998 | Kalt | 128/845 |
| 5,895,409 | A | | 4/1999 | Mehdizadeh | 606/199 |
| 6,106,544 | A | * | 8/2000 | Brazeau | 606/213 |
| 6,238,411 | B1 | | 5/2001 | Thorner | 606/199 |
| 6,318,362 | B1 | | 11/2001 | Johnson | 128/200.24 |
| 6,336,456 | B1 | | 1/2002 | Ruben | 128/206.19 |
| 6,453,901 | B1 | * | 9/2002 | Ierulli | 128/200.24 |
| 6,478,023 | B1 | | 11/2002 | Lockwood | 128/200.24 |
| 6,603,051 | B1 | * | 8/2003 | Beaudry | 602/41 |
| 6,631,714 | B2 | * | 10/2003 | Von Duyke et al. | 128/200.24 |
| 6,860,263 | B1 | | 3/2005 | Scoggins | 128/200.24 |
| 6,863,066 | B2 | | 3/2005 | Ogle | 128/200.24 |
| 6,982,359 | B1 | | 1/2006 | Beaudry | 602/54 |
| 7,022,891 | B2 | | 4/2006 | Beaudry | 602/53 |
| 7,067,710 | B1 | | 6/2006 | Beaudry | 602/54 |
| 2001/0023695 | A1 | | 9/2001 | Auriemma | 128/200.24 |
| 2002/0000227 | A1 | * | 1/2002 | Duyke et al. | 128/200.24 |
| 2003/0000521 | A1 | | 1/2003 | Beaudry | 128/200.24 |
| 2003/0005938 | A1 | | 1/2003 | Lockwood | 128/848 |
| 2004/0153019 | A1 | | 8/2004 | Beaudry | 602/42 |
| 2006/0000472 | A1 | | 1/2006 | Fenton | 128/200.24 |
| 2009/0183734 | A1 | * | 7/2009 | Kwok et al. | 128/200.24 |

* cited by examiner

*Primary Examiner*—Patricia M Bianco
*Assistant Examiner*—Ophelia Hawthorne
(74) *Attorney, Agent, or Firm*—Ronald M. Anderson (57) ABSTRACT

An adjustable nasal cavity dilator is provided that enables a user to selectively dilate a single nasal passageway in order to achieve a desired flow of air therethrough. In an exemplary embodiment, the nasal cavity dilator comprises an elongate foundation strip and a dilation adjustment band. An adhesive material secures the nasal cavity dilator to the external tissue of a user's face, on the side of the nasal cavity, and on the adjacent cheek. A fastener secures the dilation adjustment band to maintain the force that keeps the nasal cavity in the dilated state. In another embodiment, an attachment is coupled to the foundation strip in order to slidingly engage the dilation adjustment band so that it reverses direction before the force is applied. A free end of the band is then fastened to either the foundation strip or the dilation adjustment band.

27 Claims, 3 Drawing Sheets

MANUALLY ADJUSTABLE NASAL CAVITY DILATOR

BACKGROUND

In addition to providing a sense of smell, the human olfactory organ, or the nose, also serves to clean, humidify and heat the air flowing through the nose. Hair within the nasal passages retain small particles, and the mucous wetted tissue adds moisture to the air and warms cold air before it arrives in the lungs. Sometimes, a person experiences a reduction in the amount of air that can flow through the nose due to a nasal airway obstruction, for example, as a result of a deviated septum. When the skeletal and cartilaginous wall, the nasal septum, that divides the nasal cavity into two equal passageways, thereby enabling air to be drawn in, is displaced, partial blockage of one of the passageways can result. Therefore, the free flow of air is impeded through one or both of the passageways. Other nasal airway obstructions may be caused by allergies, sinus infections, or other causes of mucosal congestion such as congenital abnormalities, or trauma. Some people will experience the collapse of a nasal passageway on one side during sleep due to flaccid muscles. Regardless of the cause, even a minor obstruction of the nasal airways can hinder free breathing and thus adversely affect not only a sleep period, by causing it not to be restful or contributing to snoring, but also impair daily activities, when a person is at rest and breathing at a normal rate.

One approach currently used to address the problem of providing temporary relief of nasal airway obstruction employs a banded nasal dilator that includes an elongated band, which wraps around the back of a user's head. Each end of the band includes a face pad having an adhesive portion that is adapted to connect to the user's cheek. However, this nasal dilator does not enable the user to easily control the tension in the band so as to vary the force applied to keep the nasal cavity open, to enable easier breathing. In addition, the band that wraps around the user's head may be susceptible to displacement caused by the user's head rubbing it against a pillow, if worn overnight, for example, thereby inadvertently varying the force that tends to open the nasal cavity. Also, a user may not need to dilate both nasal airway passages. However, Scoggin's dilator is clearly designed to dilate both nasal airway passages and is not readily modified to only dilate one nasal passage.

In another known approach, an elongated substrate is used that has a top and a bottom surface and a pressure sensitive adhesive disposed on the bottom surface. A resilient member is bonded to the substrate to provide a gentle expanding force to the nasal wall tissue when the dilator is adhesively attached to the nose. However, this dilator also does not enable a user to selectively adjust the amount of dilation of the blocked nasal airway passage. Also, this dilator will dilate both nasal passages, thereby not allowing a user to correct only one airway obstruction.

The foregoing examples of related art and limitations arising therein are intended to be illustrative and not exclusive. Other limitations of the related art will become apparent to those of ordinary skill in the art upon reviewing the disclosure that follows below.

SUMMARY

A versatile nasal cavity dilator can help achieve a desired flow of air through a nasal cavity that may become at least partially obstructed if not dilated. Accordingly, such a nasal dilator was developed to address this and other problems affected by the flow of air through the nasal airways. Various embodiments of the nasal dilator enable a user to selectively adjust the amount of dilation for a single nasal airway or for each nasal airway. A user is enabled to selectively adjust the amount of dilation in one nasal airway, independent of the dilation achieved in the other nasal airway, or to separately adjust the dilation in both nasal airways.

One embodiment of the adjustable nasal cavity dilator includes an elongate foundation strip having opposed first and second ends. The ends are coupled together by an intermediate portion. An adhesive material at the first end and the second end is adapted to adhere respectively to a side of a user's nose and an adjacent portion of a user's cheek. A dilation adjustment band is attached to the foundation strip at a first point, which is adjacent to one of the first and the second ends. The dilation adjustment band is adjustable relative to a second point on the foundation strip that is spaced apart from the first point. The dilation adjustment band is adjusted before being removably secured, to provide a force between the side of the user's nose and the user's cheek that is sufficient to open the nasal airway within the user's nose to a desired extent, so as to permit the desired flow of air through the nasal airway. The dilation adjustment band is also readily readjustable by a user such that the dilation of the nasal airway can be increased or decreased. In different embodiments, the dilation adjustment band includes either a flexible strip or a flexible line. The foundation strip is also sufficiently flexible so as to substantially conform to the side of a user's nose and to a user's cheek. Optionally, the adhesive material included on the foundation strip is protected by one or more covers, which can be removed just prior to application of the adjustable nasal cavity dilator to the user's nose and cheek.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive.

Nasal Cavity Dilator

An exemplary embodiment of a versatile nasal cavity dilator in accord with the present invention enables a user to selectively dilate a nasal airway passage (or both nasal airway passages) to achieve a desired level of airflow therethrough. This dilation ensures freer flow of air through the nasal airway passage or through the entire nasal cavity if both nasal airway passages are dilated, than would often be experienced without use of the dilation. Because a partial or complete nasal obstruction may have a variety of causes, such as allergies, congestion, a deviated septum, congenital abnormalities, or trauma, and thus may cause varying amounts of blockage, it is important that a user be able to customize the extent of dilation of these passages. This customization relates not only to how far the external tissue on the nose that covers the nasal cavity is pulled to the side to open the nasal airway passage, thereby avoiding the blockage, but also relates to the side of the nasal cavity that the user desires to dilate. In some situations, it may be desirable to dilate only one side of the nasal cavity. A user adjustable device will also be more comfortable for a user who may be wearing the invention for long periods of time, such as during a sleep cycle, where it is critical to obtain rest. In contrast, a nasal cavity dilator that is unadjustable may not provide sufficient force to avoid blockage or alternatively, provide an excessive force that makes it painful to wear. In addition, a user may desire to use the nasal dilator on only one nasal passageway, because the other nasal passageway has been found not to become obstructed.

Figure 1A:
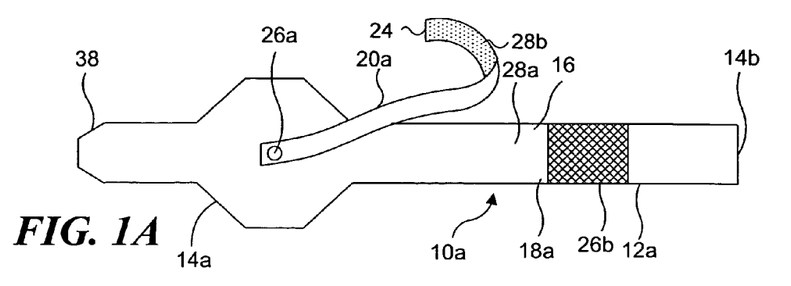
FIG. 1A is a top view of an exemplary embodiment of the adjustable nasal cavity dilator, prior to adjusting the force applied to a foundation strip with a dilation adjustment band.
Figure 2A:
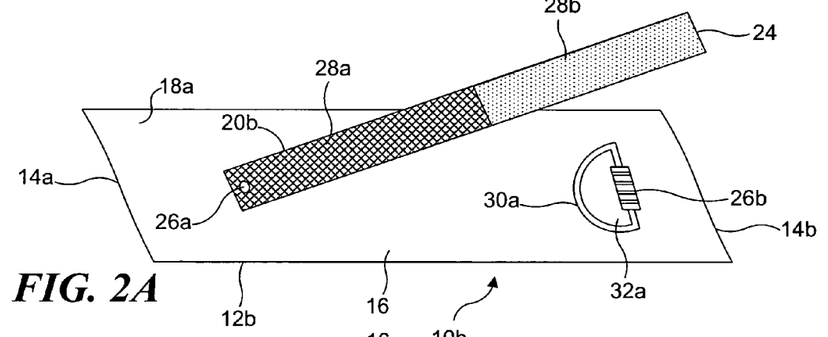
FIG. 2A is a top view of a second embodiment with an alternative elongate foundation strip and alternative dilation adjustment band, in its configuration prior to being used for adjusting the force applied to dilate a user's nasal passage.
Figure 4A:
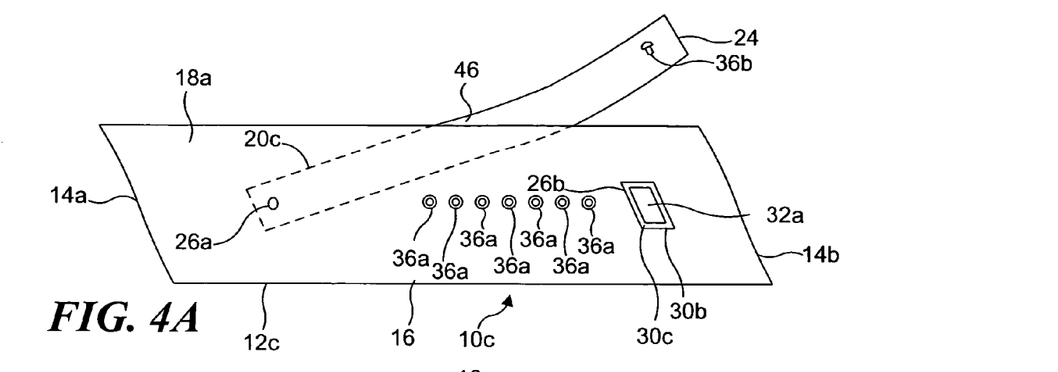
FIG. 4A is a top view of the second embodiment that illustrates yet another alternative elongate foundation strip and alternative dilation adjustment band, in an unadjusted configuration.
Figure 5A:
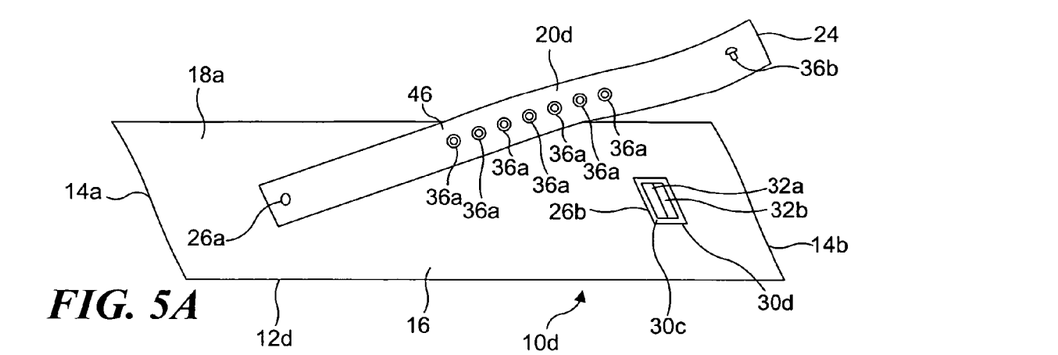
FIG. 5A is a top view of the second embodiment, illustrating a third alternative elongate foundation strip and alternative dilation adjustment band, said strip and band being shown in an unadjusted configuration.

While not limited to the embodiments that are illustrated in the drawings and discussed herein, the following discussion describes details of several different configurations or embodiments of the manually adjustable nasal cavity dilator, including four configurations of a foundation strip and four configurations of a dilation adjustment band that can be configured to form a complete manually adjustable nasal cavity dilator. By way of example, embodiments of a complete manually adjustable nasal cavity dilator includes a foundation strip 12a as shown in FIG. 1A, or a foundation strip 12b as shown in FIG. 2A, or a foundation strip 12c as shown in FIG. 4A, or a foundation strip 12d as shown in FIG. 5A. Similarly, embodiments of a manually adjustable nasal cavity dilator can include a dilation adjustment band 20a, as shown in FIG. 1A, a dilation adjustment band 20b, as shown in FIG. 2A, or a dilation adjustment band 20c, as shown in FIG. 4A, or a dilation adjustment band 20d, as shown in FIG. 5A. Those skilled in the art will realize that various configurations in addition to those illustrated are possible. For example, dilation adjustment band 20b may be configured not only with foundation strip 12b as shown in FIG. 2A, but also with foundation strip 12d. Likewise, dilation adjustment band 20d may be configured not only with foundation strip 12d as shown in FIG. 5A, but also with foundation strip 12b.

While it is particularly useful for dilating a human nasal cavity, it must be emphasized that the present invention is not limited to dilation of nasal cavities of human patients. For example, the present invention can be utilized to dilate nasal cavities of animals who experience obstructions in their nasal cavities. Also, those skilled in the art will realize that the following shapes of the foundations strips and the dilation adjustment bands are neither limited to those shown in the figures, nor are the foundation strips and the dilation adjustment bands drawn to scale.

Exemplary Embodiment of Nasal Cavity Dilator

Figure 1B:
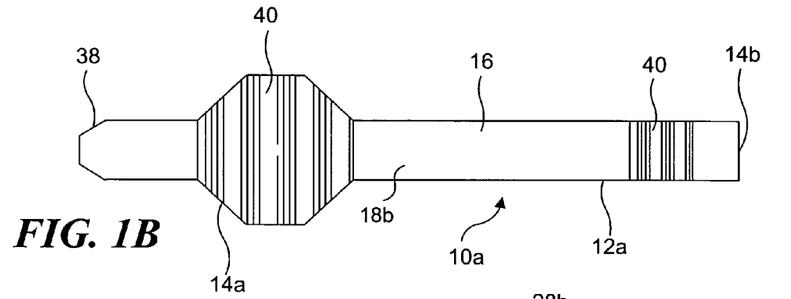
FIG. 1B is a bottom view of the embodiment of FIG. 1A.
Figure 3:
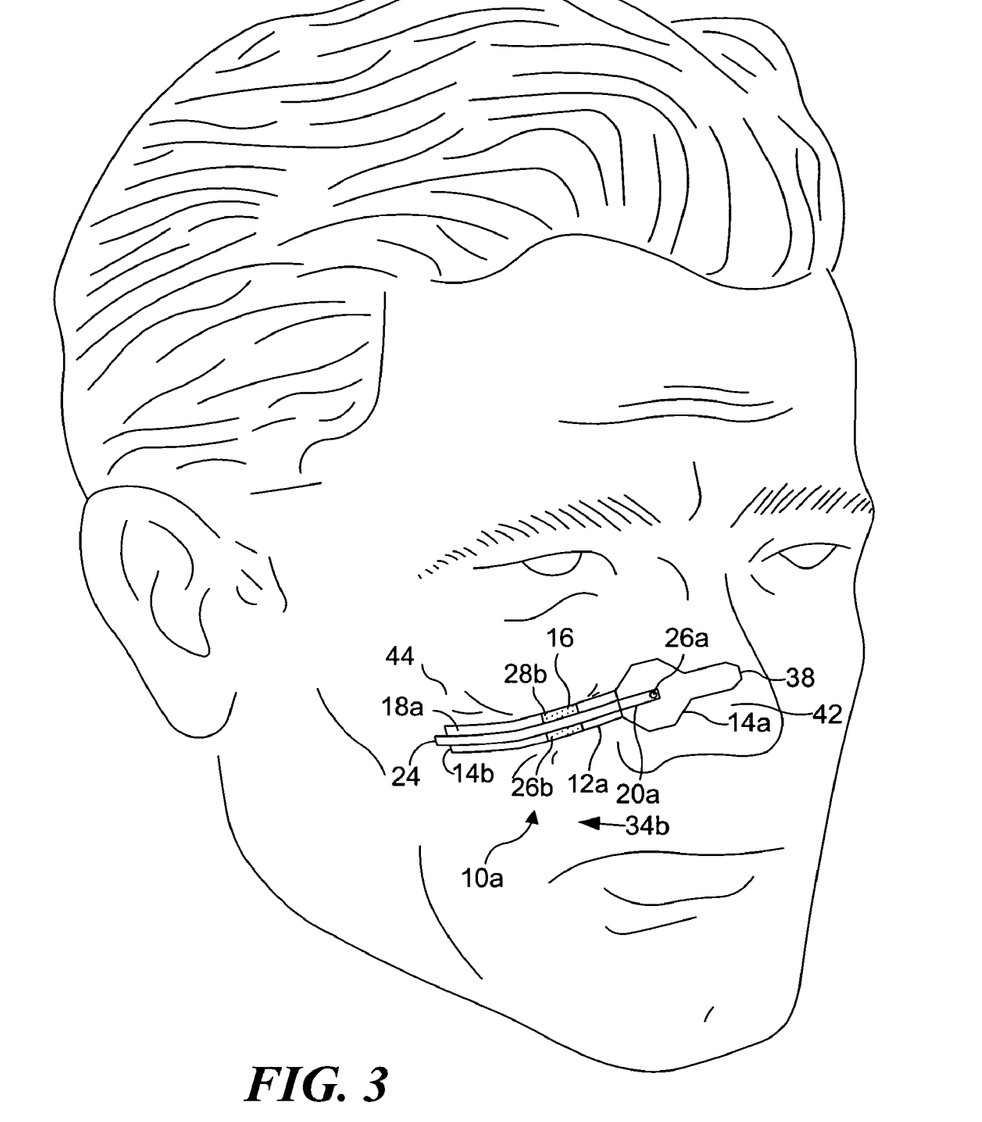
FIG. 3 is an overall view of a user's head, showing the exemplary embodiment of FIGS. 1A and 1B in its adjusted configuration, to the user's nasal airway.

FIG. 1A, FIG. 1B, and FIG. 3 illustrate an exemplary embodiment of a nasal cavity dilator 10a of the present invention. FIG. 1A that illustrates a top view of the nasal cavity dilator 10a includes foundation strip 12a shown with an outer surface 18a that is elongate in shape and that has a first end 14a and a second end 14b, wherein the ends are disposed opposite of each other. Foundation strip 12a also includes a handle 38 disposed at one of the first end and the second end, an intermediate portion 16 disposed between the first end and the second end, and one of a loop portion 28b and a hook portion 28a also disposed on outer surface 18a.

Dilation adjustment band 20a on the embodiment of FIG. 1A also has a free end 24 and an opposing end that is permanently affixed to the outer surface of the foundation strip at a first point 26a, which is disposed adjacent to one of the first end and the second end of foundation strip 12a. Although shown as a flexible strip, the dilation adjustment band could instead be a flexible line, such as a plastic line. The location of a second point 26b is spaced apart from the first point, and the dilation adjustment band is adjustable relative to the second point. Dilation adjustment band 20a also includes one of hook portion 28a and loop portion 28b, depending on which portion the foundation strip has been configured with. In other words, if the foundation strip has been configured with the hook portion, the dilation adjustment band will be configured with the loop portion so that when the foundation strip and the dilation adjustment band are positioned in contact with each other, the hook portion and the loop portion act as a fastener to hold the dilation adjustment band in a desired position that applies a desired force to the side of the nostril, removably affixing the two together. Likewise, if the foundation strip has been configured with the loop portion, the dilation adjustment band will be configured with the hook portion. As shown in FIG. 1A, hook portion 28a is disposed at second point 26b, so that when the user has pulled the dilation adjustment band with enough force to dilate the nasal airway passage sufficiently to enable a desired flow of air therethrough, the user can then press the loop portion down on an area of the foundation strip that has the corresponding hook portion. The hooks will engage the loops to maintain the desired force when the user stops pulling.

As an alternative to the hook and loop fastener, adhesive material can be used as a fastener. For example, the dilation adjustment band of FIG. 1A, can include an adhesive material instead of the hook portion. This adhesive portion will enable the dilation adjustment band to then be removably secured to the foundation strip after the force has been applied by the user to dilate the nasal air passageway as desired.

FIG. 1B illustrates a bottom view of nasal cavity dilator 10a that clearly illustrates the portions of an inner surface 18b of the foundation strip that have adhesive material applied so that the nasal cavity dilator can be temporarily secured to a user's face. First end 14a and second end 14b each include an adhesive 40 applied thereto, leaving intermediate portion 16, disposed between the first end then the second end, free of adhesive. Alternatively, adhesive can be optionally applied to the intermediate portion which may be desirable if is it necessary to substantially increase the force applied to dilate the nasal cavity or to increase the number of times that this exemplary embodiment may be repetitively used. However, a handle 38 is preferably free of adhesive so that when it is time to remove the nasal cavity dilator from a user's face, the handle, which is not adhesively secured to the user's face, may be more readily grasped by the user to facilitate gentle removal of the nasal cavity dilator from the skin. Also, it will be apparent that the handle could be located at the second end, rather than at the first end as illustrated in this exemplary embodiment.

FIG. 3 illustrates an isometric view of nasal cavity dilator 10a disposed on the user's face in an optimal position. Note that both the dilation adjustment band and the foundation strip are comprised of a material that enables them to comfortably conform to the contours and curved surface of a user's face, as shown in FIG. 3. Due to the differences in the size of noses and facial features between different individuals, the foundation strip is available in different shapes to facilitate a custom fit as evident by the different shapes illustrated in FIG. 1A and FIG. 2A.

Although the method of use will be described in detail below, note that nasal cavity dilator 10a will have one of the first end and the second end disposed on a side of a user's nasal cavity 42 that the user desires to dilate and the other and opposing end disposed on an adjacent portion of a user's cheek 44 on that side. Since the first end and the second end include an adhesive material, this adhesive material will engage the external tissue of the user's nose and cheek. First end 14a is substantially wider than the second end such that a greater portion of external tissue can be grasped by the adhesive material, thereby enabling a larger volume of the nasal cavity to be dilated because more of the skin on the side of the nose will be pulled toward the cheek when dilation adjustment band 20a is adjusted to achieve the desired force. Those skilled in the art will realize, however, that the second end could be configured to be substantially wider than the first end, the second end, or both the first and second ends can be configured to be substantially wider than the intermediate portion.

However, for all of the embodiments discussed herein, although the first point is illustrated as being proximate the first end (i.e., the first point is disposed on the side of the nasal cavity 42 (see FIG. 3)), those skilled in the art will realize that the first point may be proximate the second end, such that it is disposed proximate to the user's cheek for any embodiment. In other words, the dilation adjustment band can be secured to a first point disposed proximate to the second end, thereby resulting in the user having to apply a force generally in a direction opposite to second direction 34b, as shown in FIG. 3, in order to adjust the force on the dilation adjustment band that dilates the nasal airway passage.

Second Embodiment of Nasal Cavity Dilator

Figure 2B:
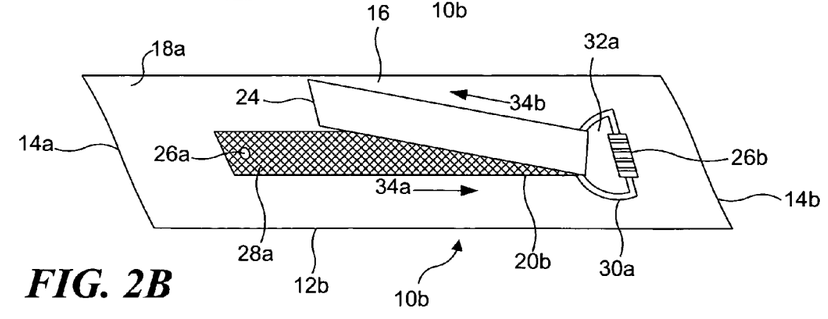
FIG. 2B is a top view of the second embodiment of FIG. 2A, illustrating the strip and the band in an adjusted configuration.
Figure 4B:
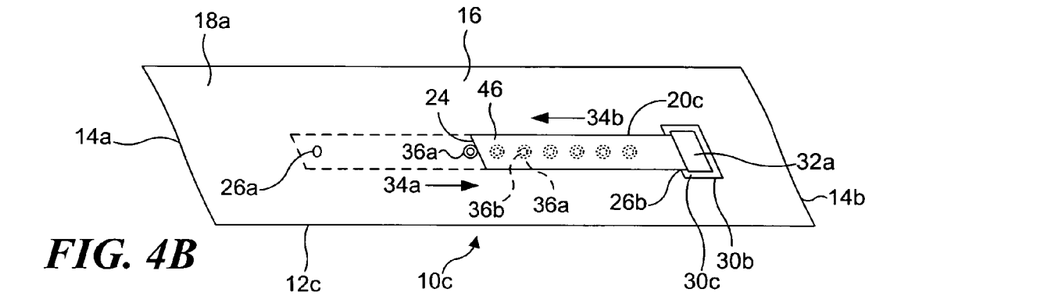
FIG. 4B is a top view of the second embodiment of FIG. 4A, illustrating the strip and the band in an adjusted configuration.

FIGS. 2A and 2B illustrate a second exemplary preferred embodiment of a nasal cavity dilator 10b of the present invention that includes an attachment, which aids in adjustment by slidingly engaging dilation adjustment band 20b of nasal cavity dilator 10b. Likewise, FIG. 4A and FIG. 4B illustrate another configuration of the second embodiment, a nasal cavity dilator 10c, in accord with the present invention that includes an alternative attachment, which aids in adjustment by slidingly engaging dilation adjustment band 20c of nasal cavity dilator 10c. Similarly, FIG. 5A and FIG. 5B illustrate yet another configuration of the second embodiment, a nasal cavity dilator 10d, in accord with the present invention that includes yet another alternative attachment, which aids in adjustment by slidingly engaging dilation adjustment band 20d of nasal cavity dilator 10d.

Figure 5B:
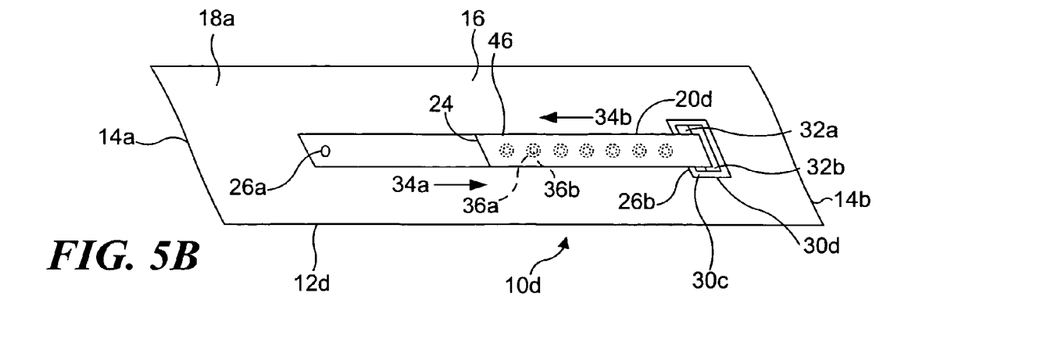
FIG. 5B is a top view of the embodiment of FIG. 5A, illustrating the strip and the band in an adjusted configuration.

FIGS. 2A, 4A, and 5A each illustrate different embodiments of the nasal cavity dilator before the dilation adjustment band has engaged an attachment and FIGS. 2B, 4B, and 5B each illustrate the nasal cavity dilator after the dilation adjustment band has engaged an attachment. In a top view, FIGS. 2A, 4A, and 5A include foundation strip 12b, foundation strip 12c, and foundation strip 12d, respectively, which are elongate in shape and are shown with outer strip 18a exposed and having first end 14a and second end 14b. Foundation strip 12b, foundation strip 12c, and foundation strip 12d include intermediate portion 16 disposed between the first end and the second end. Although not shown, as shown for foundation strip 12a in the bottom view of FIG. 1B, an adhesive is also applied to the undersurface of the first end and the second end of foundation strip 12b, foundation strip 12c and foundation strip 12d. In addition, foundation strip 12c includes an orifice 36a.

The exemplary embodiment of FIG. 2A includes an attachment ring 30a that is configured to engage dilation adjustment band 20b. Attachment ring 30a is disposed proximate to second point 26b on outer surface 18a of the foundation strip and includes a first opening 32a through which the free end of dilation adjustment band 20b can pass, so that dilation adjustment band 20b can produce the force that dilates the nasal airway. Dilation adjustment band 20b includes free end 24 and an opposing end that is permanently affixed to first point 26a, which is also disposed on outer surface 18a of one of the first end and the second end of foundation strip 12b. Dilation adjustment band 24 includes both hook portion 28a and loop portion 28b.

FIG. 2B illustrates how dilation adjustment band 20b engages attachment ring 30a. As illustrated in the top view, free end 24 is pulled in a first direction 34a, towards the attachment ring, i.e., in a direction generally away from first point 26a where the dilation adjustment band is attached. Free end 24 of the dilation adjustment band is then inserted through opening 32a of attachment ring 30a and is then pulled generally in second direction 34b (i.e., back along the foundation strip) towards first point 26a, prior to the free end being removably affixed to maintain the applied force. Because dilation adjustment band 20b is essentially folded back upon itself, loop portion 28b comes into contact with the hook portion 28a, thereby removably securing the dilation adjustment band with this hook and loop fastener. Those skilled in the art will realize that the relative positions of the loop portion and the hook portion can be reversed. For example, loop portion 28b may cover the portion of dilation adjustment band adjacent to first point 26a, and hook portion 28a may cover the rest of the dilation adjustment band, such that when the dilation adjustment band is folded back upon itself after engaging the attachment ring, the hook portion will come into contact with loop portion 28b.

Another exemplary alternative attachment comprises an attachment slot 30b that is reinforced with a grommet 30c, as shown in FIG. 4A. Attachment slot 30b is disposed proximate to second point 26b, on the foundation strip, and includes first opening 32a through which dilation adjustment band 20c can be passed. Dilation adjustment band 20c includes free end 24 and an opposing end that is permanently affixed to first point 26a on an inner surface of foundation strip 12c, adjacent to one of the first end and the second end of the foundation strip. Dilation adjustment band 20c also includes at least one protrusion 36b or at least one orifice 36a that is sized to respectively engage a corresponding orifice 36a or a protrusion 36b that is disposed on the intermediate portion of the foundation strip. As illustrated in the exemplary embodiment of FIGS. 4A and 4B, only a single protrusion 36b is provided on the dilation adjustment band, while a plurality of spaced-apart orifices 36a are provided on the foundation, so that the user can engage the single protrusion and a selected one of the plurality of spaced-apart orifices when selectively setting the force applied to the side of the user's nose to dilate the nasal airway passage. Alternatively, like the related adjustable fastener found on a plastic band on the back of many baseball caps, a plurality of spaced-apart protrusions might be provided on one of the dilation adjustment band and the foundation to engage one or more of a plurality of spaced-apart orifices on the other of the dilation adjustment band and the foundation.

FIG. 4B illustrates how dilation adjustment band 20c interacts with attachment slot 30b. As illustrated in this top view, free end 24 is pulled in first direction 34a, i.e., in a direction generally away from first point 26a where the dilation adjustment band is attached, so that an intermediate portion 46 of the dilation adjustment band extends from the first point toward the attachment slot in the first direction. Free end 24 of the dilation adjustment band is then inserted through first opening 32a of attachment slot 30b and is then pulled generally in second direction 34b towards first point 26a, i.e., in a direction that is generally opposite to first direction 34a. Because dilation adjustment band 20c includes protrusion 36b, when the dilation adjustment band 20c is essentially folded back upon itself, protrusion 36b can be inserted into any of the plurality of spaced-apart orifices 36a, which are sized to couple with protrusion 36b, thereby removably securing the dilation adjustment band to the intermediate portion such that the force applied between the first point and the second point is maintained. Those skilled in the art will realize that the relative positions of the protrusion and the selected orifice can be reversed. For example, when dilation adjustment band 20c is folded back upon, itself, if the intermediate portion of the foundation strip is configured to instead include at least one protrusion 36b and the dilation adjustment band is configured to include a plurality of orifices 36a, a selected one of orifices 36a can again couple with protrusion 36b, thereby similarly maintaining the force applied between the first point and the second point.

In addition, as shown in FIG. 5A, those skilled in the art will also realize that the dilation adjustment band may be configured to include both the plurality of orifices and the protrusion as shown in nasal cavity dilator 10d. Like the embodiment of FIG. 4A, an attachment fixture 30d (reinforced by grommet 30c) is disposed proximate to second point 26b on outer surface 18a of foundation strip 12d and includes first opening 32a such that dilation adjustment band 20d can be engaged. In addition, attachment fixture 30d is also disposed proximate to second point 26b. Dilation adjustment band 20d includes free end 24 and an opposite end that is permanently affixed to first point 26a, but on the outer surface of the foundation strip and proximate one of the first end and the second end of foundation strip 12d. Dilation adjustment band 20d also includes at least one protrusion 36b and a plurality of spaced-apart orifices 36a that are sized to engage the other of orifices 36a and a protrusion 36b, respectively.

As shown in FIG. 5B, free end 24 of the dilation adjustment band is inserted through first opening 32a of attachment fixture 30d, through a second opening 32b of attachment fixture 30d, and the dilation adjustment band is then pulled generally in second direction 34b, towards first point 26a, i.e., in a direction that is generally opposite to first direction 34a. Because dilation adjustment band 20d includes at least one protrusion 36b, when the dilation adjustment band is generally folded back upon itself, protrusion 36b can be inserted into a selected one of the plurality of spaced-apart orifices 36a, which are sized appropriately to couple with protrusion 36b, thereby removably securing the dilation adjustment band to the intermediate portion of the dilation adjustment band, so as to maintain the force applied between the first point and the second point by the user. Those skilled in the art will realize that the relative positions of the protrusion and the plurality of spaced-apart orifices can be reversed. For example, when dilation adjustment band 20d is folded back upon itself, if the intermediate portion of the dilation adjustment band is configured to instead include at least one protrusion 36b, and the free end of the dilation adjustment band is configured to include a plurality of spaced-apart orifices 36a, a selected orifice 36a can be coupled with protrusion 36b, thereby fastening the free end to the intermediate point on the dilation adjustment band and similarly maintaining the force applied by the user between the first point and the second point to dilate the nasal passageway.

As an alternative to the hook and loop fastener and the orifice and protrusion fastener, adhesive material may be used as a fastener. For example, the dilation adjustment band of FIG. 5A could include an adhesive material instead of the protrusion. This adhesive portion would allow the dilation adjustment band to then be removably secured to a different portion of the dilation adjustment band.

Third Embodiment of Nasal Cavity Dilator

Another exemplary embodiment using the nasal cavity dilator includes the step of using any two embodiments of the nasal cavity dilators, such as any of the embodiments described above, at the same time on both sides of the nasal cavity. A flexible bridging material can optionally be included to form an integral nasal cavity dilator that is intended to be used for dilating both nostrils at one time. The flexible bridging material spans a nose of a user and each end of the bridging material is coupled with one of the first end and the second end of a nasal cavity dilator disposed on the exterior of the nasal cavity. This exemplary embodiment enables a user to dilate each nasal airway separately to a different desired extent. The advantage of employing separately adjustable nasal cavity dilators is that the user can individually adjust each nasal airway passage dilation by selectively setting the force applied to dilate each nasal airway passage. For example, if a deviated septum has caused blockage of the nasal airway and this blockage is not uniform on both sides of the nasal cavity, it may be advantageous to enable a user to selectively set a different adjustment for the force applied to dilate the nasal cavity on each side of nose, to correct the blockage problem.

Method of Use

Typically, any of the exemplary embodiments of nasal cavity dilator 10a (see FIG. 3), 10b (see FIG. 2A), 10c (see FIG. 4A) and 10d (see FIG. 5A) will include one or more covers that protect adhesive 40 disposed on inner surface 18b (see FIG. 1B) of each of the foundation strip configurations and additional adhesive surfaces that act as a fastener between the dilation adjustment band and the foundation strip, and these adhesive surfaces may be disposed on the dilation adjustment bands. The cover must be peeled off the adhesive on the inner surface in order to expose the adhesive of the nasal cavity dilator and if so configured, the cover (i.e., the same or a separate cover) must also be peeled off of any adhesive portions disposed on other parts of the nasal cavity dilator. Then, the first end of the nasal cavity dilator is adhered to the external tissue on the side of the nasal cavity 42 (see FIG. 3) that is to be dilated, and the adhesive on the second end is adhered to a portion of the user's cheek on the same side of the face as the nasal cavity that it is to be dilated. If the exemplary embodiment of FIGS. 1A and 1B is used, it is advantageous to attach the substantially wider portion of the foundation to the side of the nasal cavity, as illustrated in FIG. 3, since a force can be manually applied to a larger area of the nasal cavity thereby enabling the user to dilate a larger volume of the nasal cavity.

The user will then manually apply a force to free end 24 of the dilation adjustment band and pull generally in second direction 34b, away from the nose and towards the ear on that side of the face. This force will cause the nasal airway to dilate and open. Once the force applied to cause the dilation of the nasal cavity is adjusted as desired, the user will removably secure the free end of the dilation adjustment band proximate to the second point on the foundation strip such that the force applied to dilate the nasal airway is maintained without the user continuing to apply the force. Removably securing the dilation adjustment band is accomplished in this exemplary embodiment by fastening the loop portion to the hook portion of the foundation strip such that the force that dilates the nasal cavity to the desired extent is maintained. In the alternative, the dilation adjustment band can be secured by coupling the protrusion on the dilation adjustment band with a selected one of the plurality of orifices on the foundation strip.

In the alternative, if the user is utilizing any exemplary embodiment shown in FIGS. 2A, 2B, 4A, 4B, 5A and 5B that include an attachment wherein the dilator adjustment band extends through the attachment at a position spaced apart from the fixed point, the user will engage the free end with the attachment and again pull on the free end in second direction 34b, which is generally towards the nose (if the fixed point is disposed proximate to the nose). The user will adjust the dilation adjustment band such that sufficient force is applied to the side of the nostril to dilate the nasal cavity to the desired extent. Then, the free end is removably secured such that the force that dilates the nasal cavity to the desired extent is maintained without the user continuing to apply the force. Securing the dilation adjustment band is accomplished, for example, by fastening the loop portion to the hook portion of the foundation strip as illustrated in FIG. 2B, or by fastening the protrusion on the dilation adjustment band with a selected one of the plurality of orifices on the foundation strip, as shown in FIGS. 4A and 4B, or by fastening the protrusion on the dilation adjustment band to a selected one of the plurality of orifices on the dilation adjustment band, as shown in FIGS. 5A and 5B.

If the third embodiment that facilitates simultaneous dilation of the nasal cavities (but to a separate desired extent) is being used, prior to attaching the first nasal cavity dilator on the side of the nasal cavity 42, it may be beneficial to position the bridging material over the nose to center the nasal cavity dilators and then to engage the first nasal cavity dilator on one side of the nose. After one nasal cavity dilator has been attached to the face and adjusted as described, the user simply repeats the process to adjust the second nasal cavity dilator to achieve the desired dilation of that nasal cavity.

Also note, that any of the embodiments described above may have the nasal cavity airway readjusted to a new desired extent, without removing the nasal cavity dilator from its secured position on a user's face. For example, a user may disengage the free end of the dilation adjustment band from its secured location on either the elongate foundation strip or the dilation adjustment band. Then a user may increase the force applied with the dilation adjustment band, thereby, increasing the dilation of the nasal airway from its originally dilated state or a user may decrease the force applied with the dilation adjustment band thereby decreasing the dilation of the nasal airway from its originally dilated state. While continuing to apply the increased or decreased force, a user may then secure once again, by any of the methods described above, the dilation adjustment band to either the elongate foundation strip or the dilation adjustment band at a second location. In this manner, the desired increased or decreased force has been maintained such that a new desired extent of dilation is achieved.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. An adjustable nasal cavity dilator adapted to enable a user to selectively adjustably open a nasal airway to a desired extent to ensure a free flow of air therethrough, comprising:
   (a) an elongate foundation strip having opposed first and second ends coupled together by an intermediate portion, at least the first end and the second end including an adhesive material that is adapted to adhere respectively to a side of a user's nose and an adjacent portion of a user's cheek; and
   (b) a dilation adjustment band that is fixedly attached to the foundation strip at a first point that is adjacent to one of the first and the second ends and is adjustable relative to a second point on the foundation strip that is spaced apart from the first point, the dilation adjustment band being removably attached to the foundation strip at the second point, the dilation adjustment band being adjusted before being removably secured under tension at the second point, to provide a force between the side of a user's nose and a user's cheek sufficient to open a nasal airway within a user's nose to a desired extent, so as to permit the free flow of air through the nasal airway.

2. The adjustable nasal cavity dilator of claim 1, further comprising an attachment coupled to the foundation strip at the second point, the attachment defining a first opening through which the dilation adjustment band passes, a free end of the dilation adjustment band being adapted to be pulled through the first opening defined by the attachment to produce the force that opens the nasal airway by the desired extent and then removably secured to retain the force.

3. The adjustable nasal cavity dilator of claim 2, wherein the free end of the dilation adjustment band extends from the first point toward the attachment in a first direction, passes through the first opening, and then extends back along the foundation strip in a second direction that is generally opposite to the first direction, before being removably affixed to the foundation strip to maintain the force applied between the first point and the second point, which is produced by pulling the free end of the dilation adjustment band before affixing the free end to the foundation strip.

4. The adjustable nasal cavity dilator of claim 2, wherein the dilation adjustment band includes at least one protrusion, and at least one orifice, sized to engage the at least one protrusion, and wherein an intermediate portion of the dilation adjustment band extends from the first point toward the attachment in a first direction, and the dilation adjustment band passes through the first opening and extends back along the foundation strip in a second direction that is generally opposite to the first direction, the free end of the dilation adjustment band being removably secured to the intermediate portion by engaging the orifice with the protrusion, to maintain the force applied between the first point and the second point.

5. The adjustable nasal cavity dilator of claim 1, wherein:
   (a) the intermediate portion of the elongate foundation strip includes one of:
      (i) at least one protrusion; and
      (ii) at least one orifice; and
   (b) wherein the dilation adjustment band includes the other of:
      (i) at least one orifice, sized to engage the at least one protrusion to secure the free end to maintain the force; and
      (ii) at least one protrusion, sized to engage the at least one orifice to secure the free end to maintain the force.

6. The adjustable nasal cavity dilator of claim 2, wherein the attachment comprises one of:
   (a) at least one slot formed in the foundation strip;
   (b) a ring attached to the foundation strip;
   (c) at least one grommet disposed in the foundation strip; and
   (d) a fixture attached to the foundation strip and having a second opening through which the dilation adjustment band passes.

7. The adjustable nasal cavity dilator of claim 2, wherein one of the first and second ends of the foundation strip is substantially wider than the other of the first and second ends, such that when said one end that is substantially wider is adhered to a side of a user's nose, the force is applied by the dilation adjustment band over a larger area of the side of the user's nose, enabling a larger volume of the nasal airway to be more uniformly adjustably dilated to the desired extent.

8. The adjustable nasal cavity dilator of claim 1, wherein the dilation adjustment band is readily readjustable by a user to achieve a new desired extent of dilation.

9. The adjustable nasal cavity dilator of claim 8, wherein said new desired extent of dilation is less than an extent of dilation of a nasal airway provided before readjustment of the nasal adjustment band.

10. The adjustable nasal cavity dilator of claim 1, wherein one of a hook material and a loop material comprising a hook and loop fastener is applied along an outer surface of the foundation strip through where the second point is disposed, and wherein the other of the hook material and the loop material comprising the hook and loop fastener is applied along at least a portion of the dilation adjustment band, for removably securing the portion of the dilation adjustment band to the second point on the foundation strip after the force has been applied by the dilation adjustment band between the side of a user's nose and a user's cheek.

11. The adjustable nasal cavity dilator of claim 1, wherein the dilation adjustment band comprises one of a flexible strip and a flexible line.

12. The adjustable nasal cavity dilator of claim 1, wherein a portion of the dilation adjustment band includes an adhesive material that enables the portion of the dilation adjustment band to adhere to one of:
   (a) a different portion of the dilation adjustment band; and
   (b) the foundation strip.

13. The adjustable nasal cavity dilator of claim 1, wherein the adhesive material included on one of the foundation strip and the dilation adjustment band is protected by a cover that is removable prior to use of the adjustable nasal cavity dilator.

14. The adjustable nasal cavity dilator of claim 1, wherein the foundation strip is sufficiently flexible so as to substantially conform to the side of a user's nose and to a user's cheek.

15. The adjustable nasal cavity dilator of claim 1, further comprising a handle disposed on one of the first end and the second end, wherein said handle does not include an adhesive material and provides a grippable portion that aids a user in removing the adjustable nasal cavity dilator after its use.

16. A method of adjustably dilating a nasal airway in order to achieve a desired flow of air therethrough, comprising the steps of:
   (a) adhesively adhering an elongate foundation strip so that it extends between a side of a user's nose and a user's cheek adjacent thereto;
   (b) enabling a user to apply a force between the side of the user's nose and the user's cheek by pulling on a dilator band having a first end that is attached to the foundation strip at a fixed point, the force causing the nasal airway to dilate to a desired extent so as to permit air to flow more freely through the nasal airway; and
   (c) while continuing to apply the force with the dilator band, removably securing a second end of the dilator band so as to retain the nasal airway dilated to the desired extent after the user no longer is applying force to the dilator band.

17. The method of claim 16, further comprising the step of enabling a user to disengage the second end of the dilator band from a first location disposed on one of the elongate foundation strip and the dilator band to change the force applied with the dilator band, thereby adjusting a dilation of the nasal airway to a new desired extent.

18. The method of claim 17, while continuing to apply the force with the dilator band, removably securing the second end of the dilator band at a second location disposed on one of the elongate foundation strip and the dilator band, thereby retaining the force that was changed such that the nasal airway remains adjusted to the new desired extent.

19. The method of claim 17, wherein the step of adjusting the dilation of the nasal airway to said new desired extent comprises the step of adjusting said dilation to a lesser extent of dilation.

20. The method of claim 16, further comprising the step of passing the dilator band through an attachment spaced apart from the fixed point, so that the force applied by pulling is directed between the attachment and the fixed point.

21. The method of claim 16, further comprising the step of removing at least one cover that protects an adhesive portion of the elongate foundation strip.

22. The method of claim 16, further comprising the step of removing at least one cover that protects an adhesive portion of the dilator band.

23. An adjustable nasal cavity dilator adapted to enable a user to selectively adjustably open a nasal airway to a desired extent to ensure a free flow of air therethrough, comprising:
   (a) an elongate foundation strip having opposed first and second ends coupled together by an intermediate portion, at least the first end and the second end including an adhesive material that is adapted to adhere respectively to a side of a user's nose and an adjacent portion of a user's cheek; and (b) a dilation adjustment band that is permanently affixed to the foundation strip at a first point that is adjacent to one of the first and the second ends and is adjustable relative to a second point on the foundation strip that is spaced apart from the first point, wherein one of a hook material and a loop material comprising a hook and loop fastener is applied along an outer surface of the foundation strip through where the second point is disposed, and wherein the other of the hook material and the loop material comprising the hook and loop fastener is applied along at least a portion of the dilation adjustment band, for removably securing the portion of the dilation adjustment band to the second point on the foundation strip after the force has been applied by the dilation adjustment band between the side of a user's nose and a user's cheek, enabling the dilation adjustment band to be adjusted before being removably secured to the second point, to provide a force between the side of a user's nose and a user's cheek sufficient to open a nasal airway within a user's nose to a desired extent, so as to permit the free flow of air through the nasal airway.

24. An adjustable nasal cavity dilator adapted to enable a user to selectively adjustably open a nasal airway to a desired extent to ensure a free flow of air therethrough, comprising:
    (a) an elongate foundation strip having opposed first and second ends coupled together by an intermediate portion, at least the first end and the second end including an adhesive material that is adapted to adhere respectively to a side of a user's nose and an adjacent portion of a user's cheek;
    (b) a dilation adjustment band that is attached to the foundation strip at a first point that is adjacent to one of the first and the second ends and is adjustable relative to a second point on the foundation strip that is spaced apart from the first point, the dilation adjustment band being adjusted before being removably secured to provide a force between the side of a user's nose and a user's cheek sufficient to open a nasal airway within a user's nose to a desired extent, so as to permit the free flow of air through the nasal airway; and
    (c) an attachment coupled to the foundation strip at the second point, the attachment defining a first opening through which the dilation adjustment band passes, a free end of the dilation adjustment band being adapted to be pulled through the first opening defined by the attachment to produce the force that opens the nasal airway by the desired extent and then removably secured to retain the force.

25. An adjustable nasal cavity dilator adapted to enable a user to selectively adjustably open a nasal airway to a desired extent to ensure a free flow of air therethrough, comprising:
    (a) an elongate foundation strip having opposed first and second ends coupled together by an intermediate portion, at least the first end and the second end including an adhesive material that is adapted to adhere respectively to a side of a user's nose and an adjacent portion of a user's cheek;
    (b) a dilation adjustment band that is attached to the foundation strip at a first point that is adjacent to one of the first and the second ends and is adjustable relative to a second point on the foundation strip that is spaced apart from the first point, the dilation adjustment band being adjusted before being removably secured to provide a force between the side of a user's nose and a user's cheek sufficient to open a nasal airway within a user's nose to a desired extent, so as to permit the free flow of air through the nasal airway; and
    (c) an adhesive material disposed on a portion of the dilation adjustment band that enables the portion of the dilation adjustment band to adhere to one of:
        (i) a different portion of the dilation adjustment band; and
        (ii) the foundation strip.

26. An adjustable nasal cavity dilator adapted to enable a user to selectively adjustably open a nasal airway to a desired extent to ensure a free flow of air therethrough, comprising:
    (a) an elongate foundation strip having opposed first and second ends coupled together by an intermediate portion, at least the first end and the second end including an adhesive material that is adapted to adhere respectively to a side of a user's nose and an adjacent portion of a user's cheek;
    (b) a dilation adjustment band that is attached to the foundation strip at a first point that is adjacent to one of the first and the second ends and is adjustable relative to a second point on the foundation strip that is spaced apart from the first point, the dilation adjustment band being adjusted before being removably secured to provide a force between the side of a user's nose and a user's cheek sufficient to open a nasal airway within a user's nose to a desired extent, so as to permit the free flow of air through the nasal airway; and
    (c) a cover that is applied as protection over the adhesive material included on one of the foundation strip and the dilation adjustment band and is removable prior to use of the adjustable nasal cavity dilator.

27. An adjustable nasal cavity dilator adapted to enable a user to selectively adjustably open a nasal airway to a desired extent to ensure a free flow of air therethrough, comprising:
    (a) an elongate foundation strip having opposed first and second ends coupled together by an intermediate portion, at least the first end and the second end including an adhesive material that is adapted to adhere respectively to a side of a user's nose and an adjacent portion of a user's cheek;
    (b) a dilation adjustment band that is attached to the foundation strip at a first point that is adjacent to one of the first and the second ends and is adjustable relative to a second point on the foundation strip that is spaced apart from the first point, the dilation adjustment band being adjusted before being removably secured to provide a force between the side of a user's nose and a user's cheek sufficient to open a nasal airway within a user's nose to a desired extent, so as to permit the free flow of air through the nasal airway; and
    (c) a handle disposed on one of the first end and the second end, wherein said handle does not include an adhesive material and provides a grippable portion that aids a user in removing the adjustable nasal cavity dilator after its use.

* * * * *